US00PP12501P2

(12) United States Plant Patent
Zerr

(10) Patent No.: US PP12,501 P2
(45) Date of Patent: Apr. 2, 2002

(54) POINSETTIA PLANT NAMED 'FISCOR HOT PINK'

(75) Inventor: Katharina Zerr, Simmern (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/209,754

(22) Filed: Dec. 11, 1998

(51) Int. Cl.[7] ..... A01H 5/00
(52) U.S. Cl. ..... Plt./307
(58) Field of Search ..... Plt./307, 306

(56) References Cited

PUBLICATIONS

UPOV–ROM GTITM Computer Database 1999/02, GTI JOUVE Retrieval Software, citations for 'Fiscor Hot Pink', May 1999.*

German Application—FISCOR HOT PINK—Dec. 15, 1997.

German Denomination—FISCOR HOT PINK—Aug. 15, 1998.

Canadian Application—FISCOR HOT PINK—Aug. 18, 1997.

Fischer Poinsettia Catalogue—Germany (1998), p. 20 (FISCOR HOT PINK).

* cited by examiner

*Primary Examiner*—Bruce R. Campell
*Assistant Examiner*—Michelle Kizilkaya
(74) *Attorney, Agent, or Firm*—Foley & Lardner

(57) ABSTRACT

'Fiscor Hot Pink' is characterized by uniform rose-red bract color (RHS 52A); medium-sized, flat involucre with moderately lobed bracts; intense dark-green foliage with weak lobes; compact and low, relatively wide plant habit; medium to early flowering response; and relatively good keeping quality of bracts and foliage.

1 Drawing Sheet

BACKGROUND OF THE INVENTION

The present invention relates to a new and distinct cultivar of Poinsettia plant known by the cultivar name 'Fiscor Hot Pink' and botanically known as *Euphorbia pulcherrima*.

'Fiscor Hot Pink' is a product of a mutation induction breeding program carried out by the inventor, Katharina Zerr, in Hillscheid, Germany, in 1994. The primary objective of the induction program was to expand the bract color ranges of 'Fiscor' (U.S. Plant Pat. No. 9,364). 'Fiscor' is characterized by its relatively dark-red colored bracts with dark-green foliage and comparatively compact habit.

The irradiation program comprised exposing rooted cuttings taken from plants of the parent cultivar to an X-ray source of 30 Gy dosage in Ahrensburg, Germany, under the supervision of the inventor. The irradiated plants were grown out in a greenhouse and were asexually propagated, in Hillscheid, Germany, by the inventor by taking cuttings. The plants resulting from these cuttings were screened for mutations as small, flowering, single-stem plants beginning in autumn of 1994 and continuing thereafter. The mutations discovered were identified by numbers. Parts of plants exhibiting a mutation of interest were left to develop vegetative shoots which were used as cuttings and grown out.

'Fiscor Hot Pink' originated from a single plant (No. 499) having rose-red/carmine-red bracts, which was discovered in the summer of 1995. It was propagated vegetatively by taking cuttings, and the offspring were screened for uniformity in spring of 1996 prior to further propagation. The clone was examined more closely in autumn of 1996, and again in the late summer and autumn of 1997. Horticultural examination of the clone starting in 1997 and continuing thereafter has confirmed that the combination of character istics as herein disclosed for 'Fiscor Hot Pink' are firmly fixed and retained through successive generations of asexual reproduction.

BRIEF DESCRIPTION OF THE INVENTION

The following traits have been repeatedly observed and are determined to be basic characteristics of 'Fiscor Hot Pink' which in combination distinguish this Poinsettia as a new and distinct cultivar:

1. Uniform rose-red bract color;
2. Medium-sized, flat involucre with moderately lobed bracts;
3. Intense dark-green foliage with weak lobes;
4. Compact and low, relatively wide plant habit;
5. Medium to early flowering response; and
6. Relatively good keeping quality of bracts and foliage.

'Fiscor Hot Pink' has not been observed under all possible environmental conditions. The phenotype may vary significantly with variations in environment such as temperature, light intensity, and daylength without any change in the genotype. The following observations, measurements and comparisons describe plants grown in Langley, British Columbia, Canada, under greenhouse conditions which approximate those generally used in commercial practice.

Of the many commercial cultivars known by the inventor, the most similar in comparison to 'Fiscor Hot Pink' are the parent cultivar 'Fiscor' and the patented cultivar 'Fiscorosa' (U.S. Plant Pat. No. 10,077). In comparison to 'Fiscor', 'Fiscor Hot Pink' has a lighter, and slightly more bluish hue in bract color. The difference in bract color between the cultivars is best visible under relatively warm growing conditions and diminishes at cool temperature and high light intensity.

In comparison to 'Fiscorosa', 'Fiscor Hot Pink' has more intensely colored and more uniformly colored bracts. There is only a small difference in color between the primary bracts and the smaller younger bracts. Due to the intense coloring of the lower bracts, 'Fiscor Hot Pink' is marketable a few days earlier than 'Fiscor' or 'Fiscorosa', although the general development of the true flowers (the cyathia) is not different.

BRIEF DESCRIPTION OF THE DRAWING

The accompanying color photographic sheet shows typical inflorescence and foliage of a mature potted plant of 'Fiscor Hot Pink', with colors being as true as possible with illustrations of this type.

DETAILED BOTANICAL DESCRIPTION

The plants described were grown in a greenhouse in Langley, British Columbia, Canada, in autumn of 1997. Rooted cuttings were planted into 15-cm pots on August 1, and were pinched on August 18, leaving 8 nodes. The minimum temperature was 23° C. until October 10, 20° C. to mid-November, and lower thereafter. The plants initiated flowers under natural short-day conditions in autumn.

Observations and measurements were mainly taken at the beginning of flowering. In the following description, color references are made to The Royal Horticultural Society Colour Chart (R.H.S.). The color values were determined indoors in a north light.

Classification:

*Botanical.*—*Euphorbia pulcherrima.*

*Commercial.*—Poinsettia, cv. 'Fiscor Hot Pink'.

Parentage: Induced mutation of 'Fiscor'.

Plant:

*Form.*—Shrub, self-branching.

*Growth habit.*—Moderately compact, weak to medium growth; pinched plants are bushy and relatively wide. Height, including pot, is 41 cm. The average number of branches is 8.8.

*Stem color.*—Light to medium-green, with weak infusion of anthocyanin.

*Rooting.*—Medium, about 20–24 days.

*Blooming habit.*—Flowering response time under natural short-day conditions in autumn: botanically, cyathia open, around December 1; commercially, bracts colored and marketable, in late November.

*Flowering response time.*—About 9.5 weeks.

*Keeping quality.*—For approximately 4 weeks or more, plants show no tendency towards fading or drooping and good retention of foliage and bracts.

Foliage:

*Shape.*—Broad elliptical, with rounded or slightly wedge-shaped base, weak lobes, and acuminate tip.

*Margin.*—Entire.

*Texture.*—Upper surface: Smooth and flat, only weakly veined, color of veins is about RHS 146 D or lighter; the basal part of midrib has the same red coloring as the petiole. Lower surface: Flat and smooth, except for the slightly protruding midrib and finer side veins which are arranged in a herringbone pattern; the vein color is a very light green, RHS 145 C.

*Size.*—Leaf blade length is 13.2 cm; leaf blade width is 8.7 cm; petiole length is 7.5 cm.

*Color.*—Generally a uniform dark-green. Mature foliage: Upper surface is RHS 139 A; under surface is R.H.S. 137 B. New foliage: Upper side is about RHS 143 A; under side is about RHS 137 D.

*Petiole color.*—Red to dark-red, near RHS 53 B (Fiscor — RHS 53 A).

*Aspect.*—Petioles and leaf blades are horizontally directed.

*Disease resistance.*—Typical, no special observations made.

Flowering description:

*Inflorescence.*—Almost flat and horizontally directed, with the bracts in overlapping arrangement with a well-closed center already at the beginning of flowering. The diameter of inflorescence is 23 cm.

*Number of inflorescence per plant.*—Approximately 6.5–7.0.

*Number of bracts per inflorescence.*—9–11 true bracts, each over 2 cm in length.

*Size of bract.*—The largest completely colored bract has a length of 12.7 cm and a width of 9.3 cm; petiole is 2.0 cm.

*Bracts, shape.*—Ovate-shaped, with rounded base, acuminated tip, and with weak lobes; the smaller, younger bracts are broad elliptically shaped and usually without lobes.

*Texture.*—Flat and smooth, almost no rugosity, the veins are arranged in a herringbone pattern and are hardly visible; on the upper surface, the color of the veins corresponds to the bract color or appears slightly darker, while the veins on the lower surface are usually lighter, brownish-pink, about RHS 47 B or lighter.

*Color.*—Generally an intense rose-red, uniform, and without tendency to fading near the margin. Upper surface: Near RHS 52 A ('Fiscor' — RHS 46 B, 'Fiscorosa' — RHS 51 B — RHS 52 B). Lower surface: RHS 52 A to B.

*Petiole, color.*—Reddish, about RHS 53 C.

*Cyathia.*—Few, about 10 in a narrow cluster, about 20 to 25 mm wide; diameter of the single cyathium is 6 mm.

*Color.*—Mainly light-green, R.H.S. 143 C, with medium-green patches, about RHS 137 D; top is reddish, between RHS 46 C and RHS 52 A.

*Retention.*—Average.

*Nectar cups.*—Small to medium-sized, golden yellow, usually no anthocyanin coloring near margin.

Reproductive organs:

*Stamens.*—Red filaments, fertile, yellow pollen.

*Pistils.*—Style and stigma are red, 6-lobed stigma.

*Ovaries.*—Triangular, 3 ovules.

*Fruit/Seed set.*—Few seeds are formed spontaneously but are fertile when pollinated; shape and development of the seeds are typical of the species.

I claim:

1. A new and distinct poinsettia plant named 'Fiscor Hot Pink', substantially as illustrated and described.

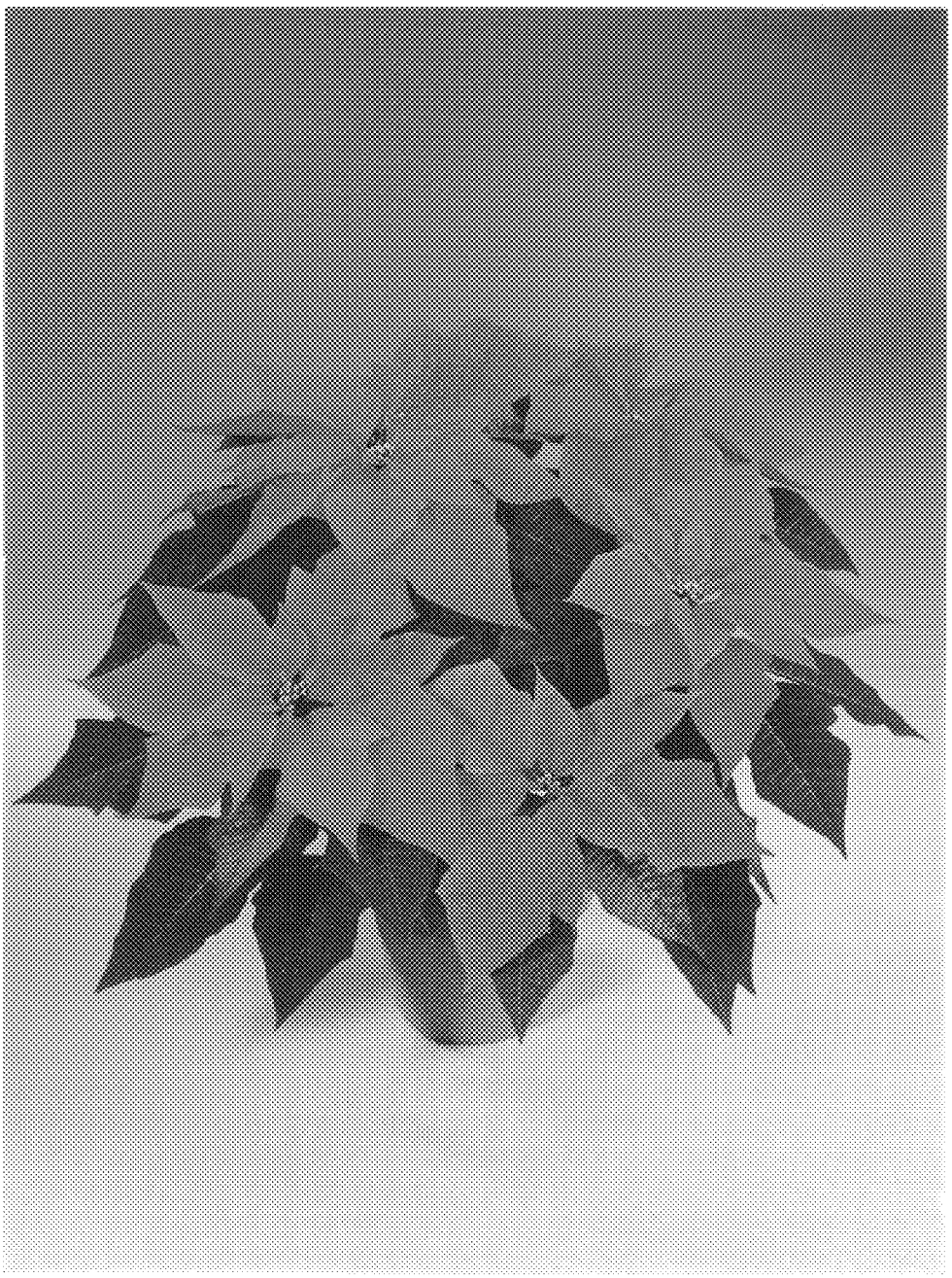

* * * * *